US010729577B1

(12) United States Patent
Alsiddiky et al.

(10) Patent No.: US 10,729,577 B1
(45) Date of Patent: Aug. 4, 2020

(54) HIP SPICA CAST APPLICATION DEVICE

(71) Applicant: KING SAUD UNIVERSITY, Riyadh (SA)

(72) Inventors: Abdulmonem Alsiddiky, Riyadh (SA); Raheef Mohamed Alatassi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/566,984

(22) Filed: Sep. 11, 2019

(51) Int. Cl.
*A61F 5/37* (2006.01)
*A61F 5/058* (2006.01)

(52) U.S. Cl.
CPC .......... *A61F 5/3776* (2013.01); *A61F 5/0585* (2013.01)

(58) Field of Classification Search
CPC . A61F 5/3776; A61F 5/0585; A61G 13/1245; A61G 13/123; A61G 13/125; A61G 7/075; A61G 7/0755; A47C 16/02; A47C 16/025; A47C 7/503; A47C 7/506; A47C 7/50
USPC .......................................................... 602/8
See application file for complete search history.

(56) References Cited

U.S. PATENT DOCUMENTS

| | | | |
|---|---|---|---|
| 3,766,384 A | 10/1973 | Anderson | |
| 4,527,555 A | 7/1985 | Ruf | |
| 4,940,218 A * | 7/1990 | Akcelrod | A61G 13/0036 5/621 |
| 5,802,641 A * | 9/1998 | Van Steenburg | A61G 13/0009 5/602 |
| 6,634,043 B2 * | 10/2003 | Lamb | A61G 13/0036 297/71 |
| 7,669,262 B2 | 3/2010 | Skripps et al. | |
| 8,001,633 B2 * | 8/2011 | Swain, Jr. | A61G 13/12 5/621 |
| 10,188,571 B2 | 1/2019 | Wyslucha et al. | |
| 10,265,236 B1 | 4/2019 | Alsiddiky et al. | |
| 2004/0133979 A1 * | 7/2004 | Newkirk | A61G 13/0036 5/600 |
| 2007/0251011 A1 * | 11/2007 | Matta | A61G 13/0036 5/624 |
| 2008/0214976 A1 | 9/2008 | Memminger | |
| 2013/0199541 A1 * | 8/2013 | Sluss | A61G 15/12 128/845 |
| 2014/0068864 A1 * | 3/2014 | Clark | A61G 13/101 5/621 |
| 2015/0245971 A1 | 9/2015 | Bernardoni et al. | |

* cited by examiner

*Primary Examiner* — Tarla R Patel
(74) *Attorney, Agent, or Firm* — Richard C. Litman; Nath, Goldberg & Meyer

(57) ABSTRACT

A hip spica cast application device for holding a patient's legs in a desired position while a spica cast is applied. The device includes an adjustable vertical post extending out of a base. Two extendable arms are pivotally attached to the top of the post. Each arm has a "U"-shaped leg holder at one end to receive and support a patient's thigh. A platform extends from a top of the vertical post for engagement with a table, such as a surgical table. During a hip spica casting procedure, the post length, arm length, and arm angles can be adjusted and locked in place to support and maintain the patient's legs at a desired position.

6 Claims, 8 Drawing Sheets

HIP SPICA CAST APPLICATION DEVICE

BACKGROUND

1. Field

The disclosure of the present patent application relates to orthopedic instruments, and particularly to a hip spica cast application device.

2. Description of the Related Art

A hip spica is a specific form of cast or plaster that is usually used for children who have had to undergo a hip reduction procedure to treat developmental hip dysplasia. The hip spica is also used in the treatment of other pediatric orthopedic traumas and conditions, such as post-operative immobilization following reconstructive hip procedures, urologic bladder extrophy procedures, femur fractures, pelvic fractures, and various hip soft tissue release-type procedures.

The hip spica cast can maintain the position of the reduced hip in a desired position for a period of time and prevents movement in the hips. Generally, two physicians are required to apply the cast. The first physician holds the lower extremities in reduced position so the hips do not lose the reduction. The second physician wraps the cast around the hip and lower extremities while they are held in the reduced position.

Usually, the cast takes time to dry and solidify into the final shape. During this period, the physician who holds the lower extremities may become fatigued and exhausted. Moreover, the risk of changing the position of the reduced hips increases and the optimal final result of the operation lessens.

In addition to the challenges faced by the physicians during application of the cast, the tables currently used for spica application are large in size and are difficult to store and retrieve for use.

Thus, a hip spica cast application device solving the aforementioned problems is desired.

SUMMARY

The hip spica cast application device according to the present teachings is configured for holding a patient's legs in a desired position during application of a spica cast. The device includes an adjustable vertical post extending out of a base. Two extendable arms are pivotally attached to the top of the post. Each arm has a "U"-shaped leg holder at one end to receive and support a patient's thigh. A platform extends from a top of the vertical post for engagement with a table, such as a surgical table. During a hip spica casting procedure, the post length, arm length, and arm angles can be adjusted and locked to support and maintain the patient's legs at a desired position. The device can also be used for holding the patient's lower extremities before the procedure to facilitate sterilization and draping.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
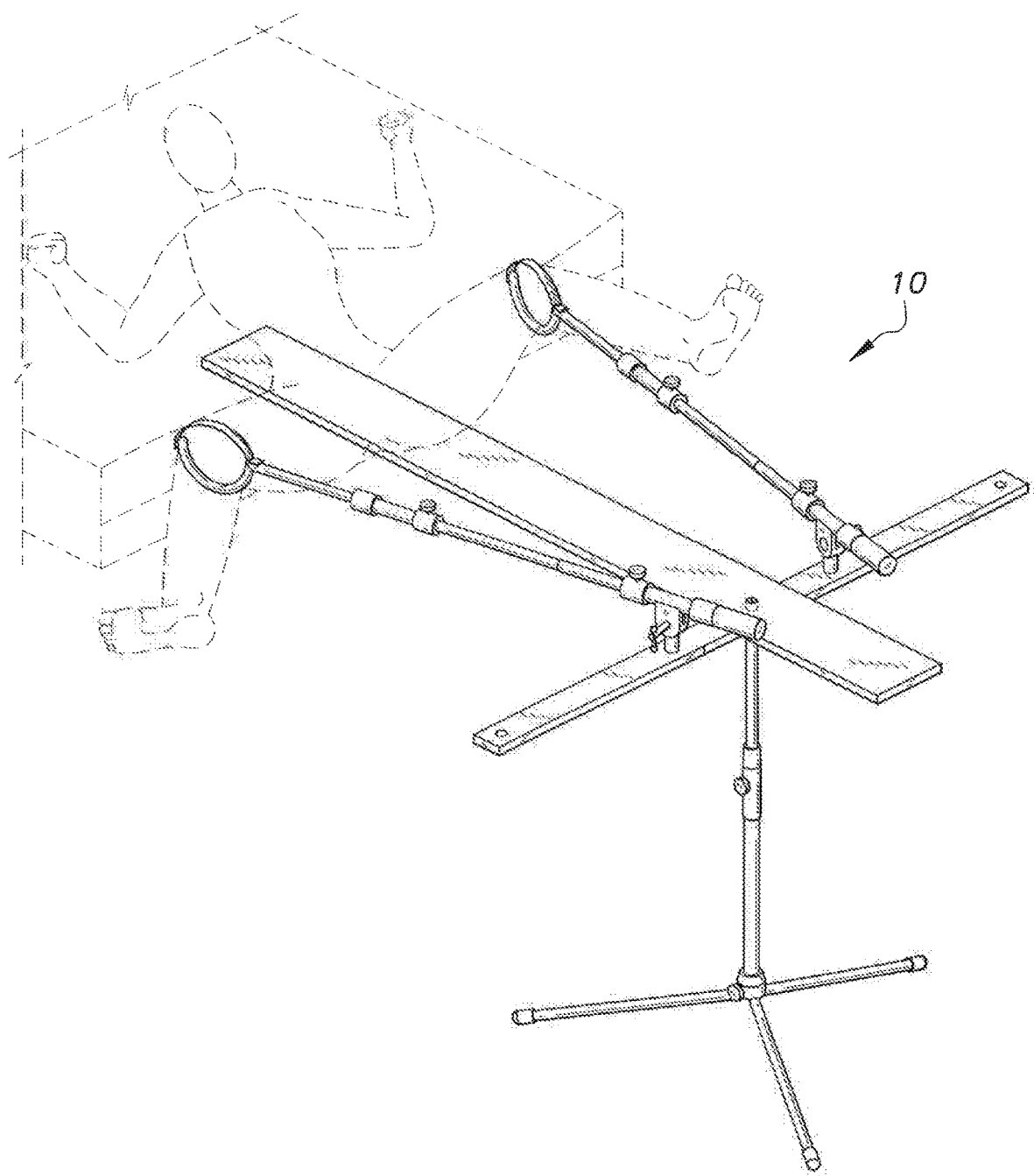
FIG. 1 is an environmental, perspective view of a hip spica cast application device.
Figure 2:
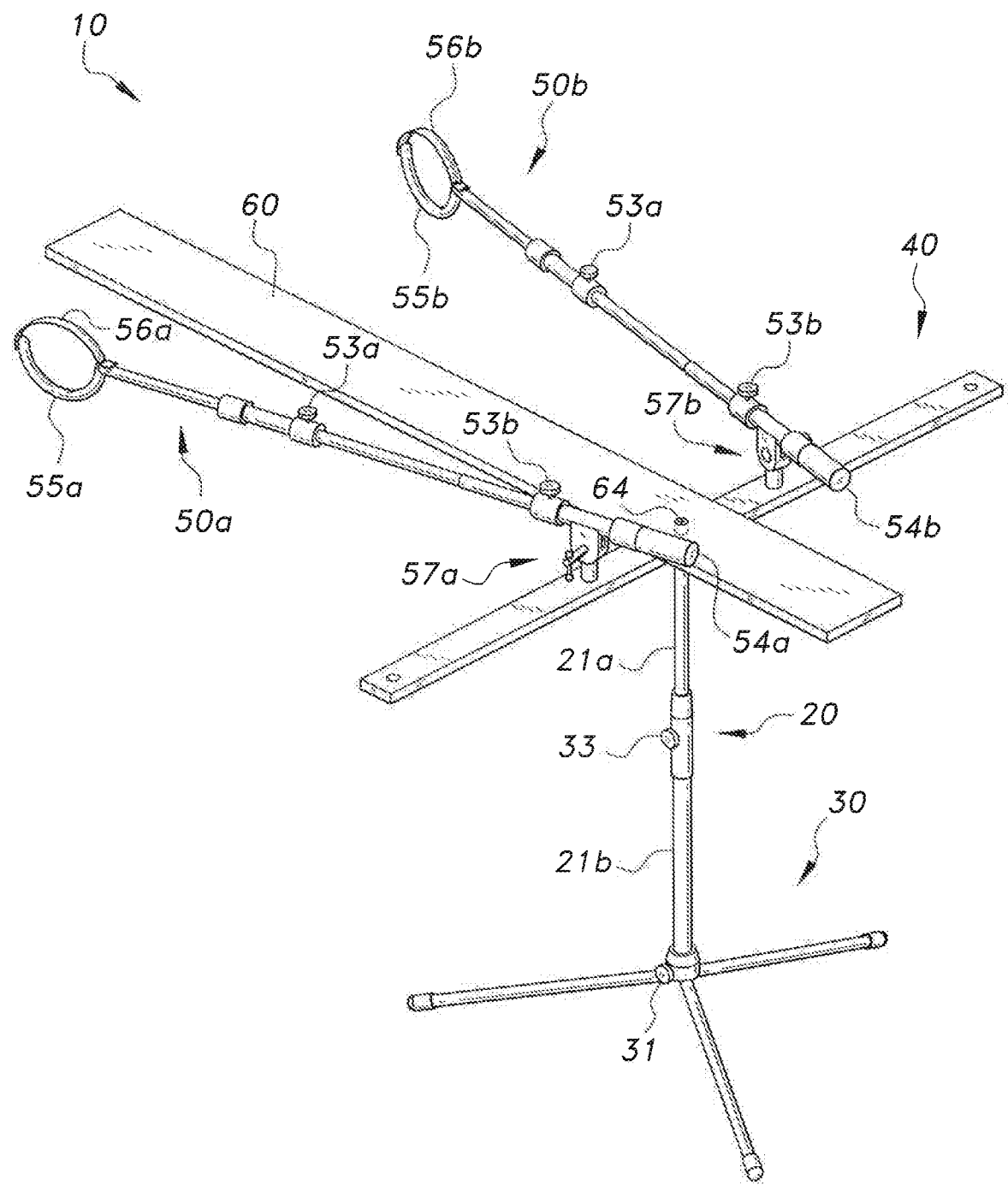
FIG. 2 is a perspective view of a hip spica cast application device.
Figure 8:
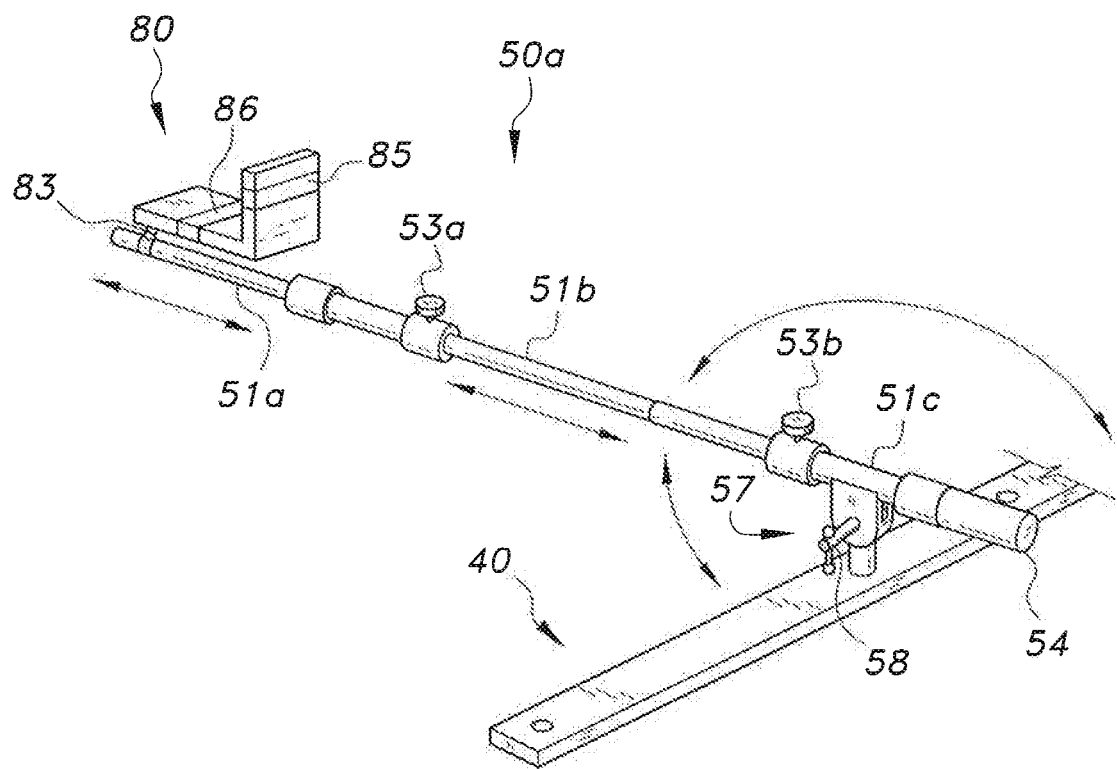
FIG. 8 is a perspective view of one arm of the hip spica cast application device showing a second embodiment of a leg holder.

FIG. 1 shows an embodiment of the hip spica cast application device. The device 10 is configured for holding a patient's legs in a precise position while a spica cast is applied. As shown in FIG. 2, the device 10 generally includes a base 30, a telescopic post 20 extending from the base 30, a horizontal support member 40 affixed to a top end of the post 20, a platform 60 attached to the horizontal support member 40 directly above the telescopic post 20, and a pair of spaced, telescopic arms 50a, 50b pivotally attached to the horizontal support member 40. An end of each arm has a holder configured to receive and secure a patient's thigh therein. In an embodiment 60, the platform 60 can be detachably attached to the horizontal support member 40. In an embodiment, each arm has a U-shaped holder, as shown in FIG. 2. In an embodiment, each arm as an L-shaped holder as shown in FIG. 8.

The base 30 can include a plurality of radially extending legs, e.g., three legs, for positioning on a floor or horizontal support surface and supporting the post 20 in a stable manner. Alternatively, the base may include a wide plate. Additionally, the base 30 may include wheels (with or without built-in brakes) to facilitate movement. Heavy materials may be used or additional weight may be added to the base 30 in order to further stabilize the device 10 by lowering the center of gravity. The base 30 may be radially extendable, to allow added support for heavier patients and facilitate storage. In an embodiment, legs of base 30 may be telescoping. In an alternative embodiment, a base plate may include extendible, folded portions which can be unfolded or extended to widen the base and folded when not needed.

The post member 20 has an adjustable length. The length can be adjusted to accommodate the height of a surgical table 70. In an embodiment, the post member 20 includes an inner post member 21a and an outer post member 21b that telescopically receives the inner post member 21a. A locking screw 33 threadedly engages the outer member 21b. The screw 33 can be tightened to contact and push against the inner post member 21a to thereby lock the inner post member 21a at a fixed position. Loosening the screw 33 releases the inner post member 21 and allows the inner post member 21 to move up or down as desired. As such, the height of the post member 20 can be adjusted by lifting or lowering the inner member 21a to a desired position and then locking it at that position by tightening the screw 33. It is also contemplated that the telescoping mechanism 21 is hydraulically operated and thus adjusted through the addition or removal of a hydraulic fluid. Hydraulic operation may be advantageous when adjustment is needed while the weight of the patient is resting on the device. It should be understood that the configuration of the post member 20 is not limited to concentrically aligned members, and may include other adjustable configurations, e.g., a first post member slidably engaging an outer wall of a second post member. The telescoping mechanism may include three or more members to increase adjustability. It should further be understood that the locking mechanism is not limited to a screw, and can include any locking mechanism known in the art for telescoping members, for example a taper lock.

The horizontal member 40 can be rigidly attached to a top end of the post member 20. The horizontal member 40 can extend normal to the post member 20. The horizontal member 40 is pivotally secured to two arms 50a, 50b. Hinges 57a, 57b connect each arm 50a, 50b to the horizontal member 40. The hinges 57a, 57b give the arms 50a, 50b the ability to be individually pivoted. Locking levers 58 allow a user to lock the hinges at a set position. Accordingly, a user will be capable of adjusting the arms 50a, 50b to any particular angular position desired for the procedure. Through use of the locking levers 58, the hinges 57a, 57b can be locked in the set position for the entirety of the procedure, or until the user desires a different position.

Figure 4:
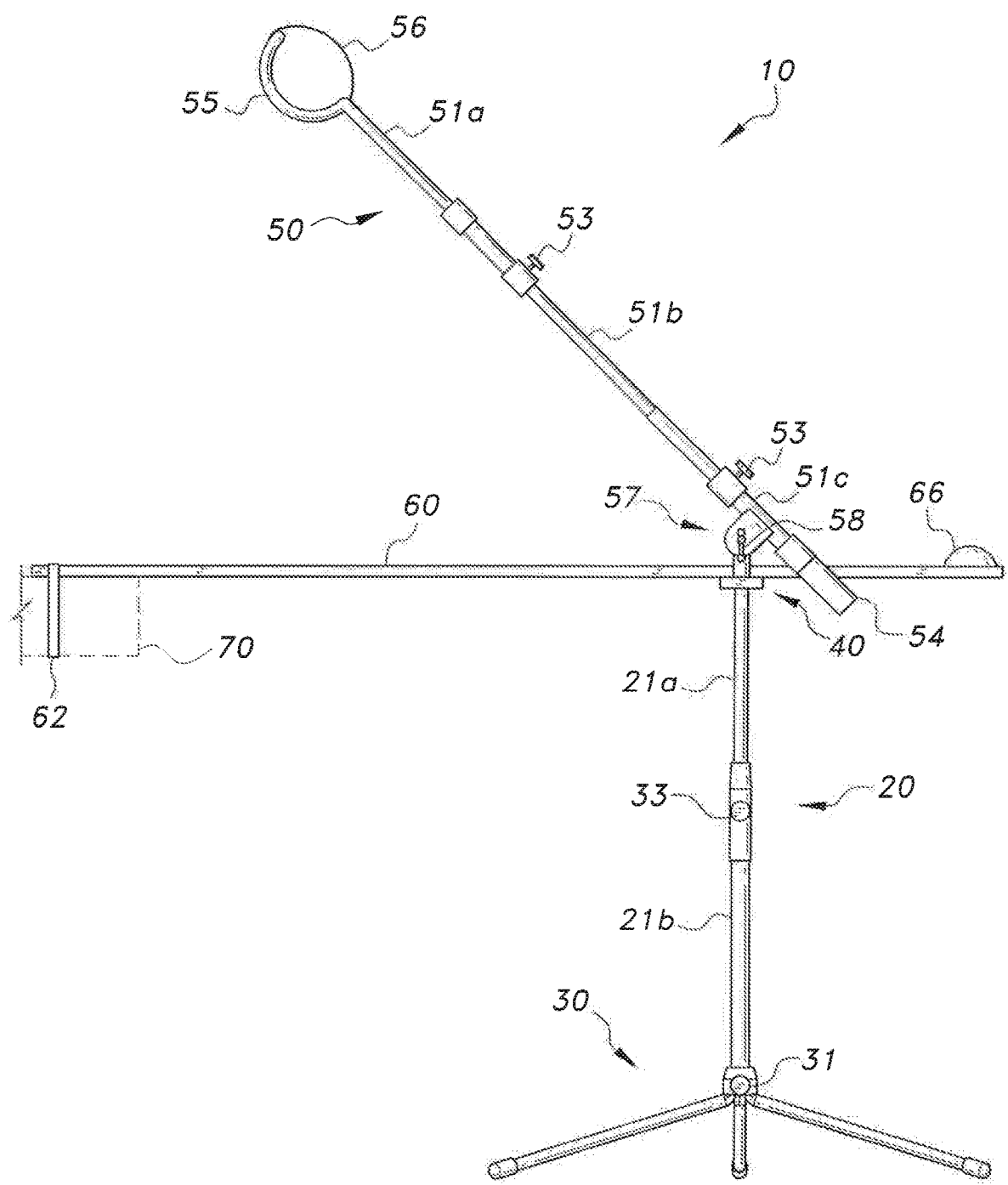
FIG. 4 is an isometric side view of the hip spica cast application device in a casting position.

The platform 60 can be rigidly or detachably attached to the horizontal member 40. In an embodiment, the platform 60 can be attached to the top of the horizontal member 40 directly above the post member 20 using screw 64 which extends though the platform 60 and engages a threaded hole defined within the horizontal member 40. In an embodiment, the screw 64 has a handle at a top end thereof to facilitate tightening or loosening the screw 64. In other embodiments, the platform 60 may be connected to the horizontal member 40 via any known method in the art. The platform 60 may be connected to a mid-portion of the horizontal member 40. In the non-limiting embodiment shown in FIG. 2, about one quarter of the platform 60 extends beyond a first edge the horizontal member 40, defining a platform short side, with the remaining three quarters extending beyond an the opposing second edge of the horizontal member 40, defining a platform long side. The short side may be configured to counterbalance the long side. For example, a thickness of the platform 60 may be greater on the short side than the long side or a weight 66 may be added to the short side (as shown in FIG. 4). The platform 60 can be made from any suitable material, including wood, plastic, acrylonitrile butadiene styrene polymer, or glass. For example, the platform 60 can include melamine or processed wood. Preferably, the platform 60 is radiolucent. In an embodiment, the platform is rectangular, having height ranging from about 1 cm to about 2 cm, and a depth ranging from about 8 cm to about 12 cm. In an embodiment, the platform is rectangular, with curved or beveled edges. In use, the platform end at the long side of the platform 60 may be rested on a surgical table 70. Once on the table 70, the platform 60 can provide support for the patient's buttock and lower back, as well as provide additional stability to the device 10 for preventing tipping.

The length of each arm 50a, 50b is individually adjustable which gives a user the ability to move leg holders 55a, 55b of the arms 50a, 50b towards or away from the horizontal member 40. The embodiment shown in FIG. 1 includes arms 50a, 50b that telescope similar to the post member 20. Each arm 50a, 50b includes an inner member 51a that slides within an intermediate member 51b. A first screw 53a, which is threaded into the intermediate member 51b, may be screwed in to push against the inner member 51a and lock it in place. Similar to the post member 20, the arms may be hydraulically operated. The arms may also include an outer member 51c that has a telescopic relationship with intermediate member 51b. Intermediate member 51b is capable of sliding in and out of the outer member 51c. Second screw 53b can be tightened to contact outer member 51c and thereby lock intermediate member 51b at a desired position. An opposing end of each arm 50a, 50b, includes a handle 54a, 54b that may be held by a user for adjusting the angle of the arm. Similar to the telescopic post member 20, the arms 50a, 50b are not limited to concentrically aligned members, and may instead include any suitable configuration that permits slidable engagement of the first member and the second member. Each arm may include two or more members, e.g., three members. The locking mechanism is not limited to a screw, as any appropriate locking feature known in the art is contemplated, for example a taper lock.

In a preferred embodiment, leg holders 55a, 55b are located at an end of the arms 50a, 50b. The leg holders 55a, 55b may be "U"-shaped, as seen in FIG. 2. The leg holders 55a, 55b are sized to receive and secure a user's leg thereto. It is contemplated that the leg holders 55a, 55b may be detachable and replaced with other leg holders of a different size or shape, or have adjustable sizes to accommodate different sized patients. Since the patient will be held by the cast application device 10 for a prolonged period of time, a pad may be secured to the inner portion of the leg holders 55a, 55b. A strap 56 may extend across the open portion of the "U" to further secure the patient's leg, as seen in FIG. 1. The strap 56 may prevent the leg from sliding down over time, thereby preventing the hip from becoming misaligned mid-procedure. A high friction coating may be applied to the user contacting portion of the holder to further prevent sliding.

In an alternative embodiment, each arm 50a, 50b, can have IL-shaped leg holders 80, as shown in FIG. 8. Each leg holder 80 can be connected to the inner member 51a by a locking joint 83. In some cases, the "L" shape may be preferable for providing support to a patient's ankles. The locking pivot allows the practitioner to pivot the leg holder 80. The joint 83 may be a ball and socket joint, a double hinge joint, or any joint known in the art that can provide single or multiple degrees of freedom and can be locked at a set position. Similar to the "U" shaped leg holder 55, the "L" shaped leg holder 80 may have a padded inner surface for patient comfort. A first strap 85 may be used to wrap around a patients foot and a second strap 86 may be used to wrap around a patient's ankle. The first and second strap may be secured using hook and loop fasteners, belt like holes and a buckle, or cords.

Figure 3:
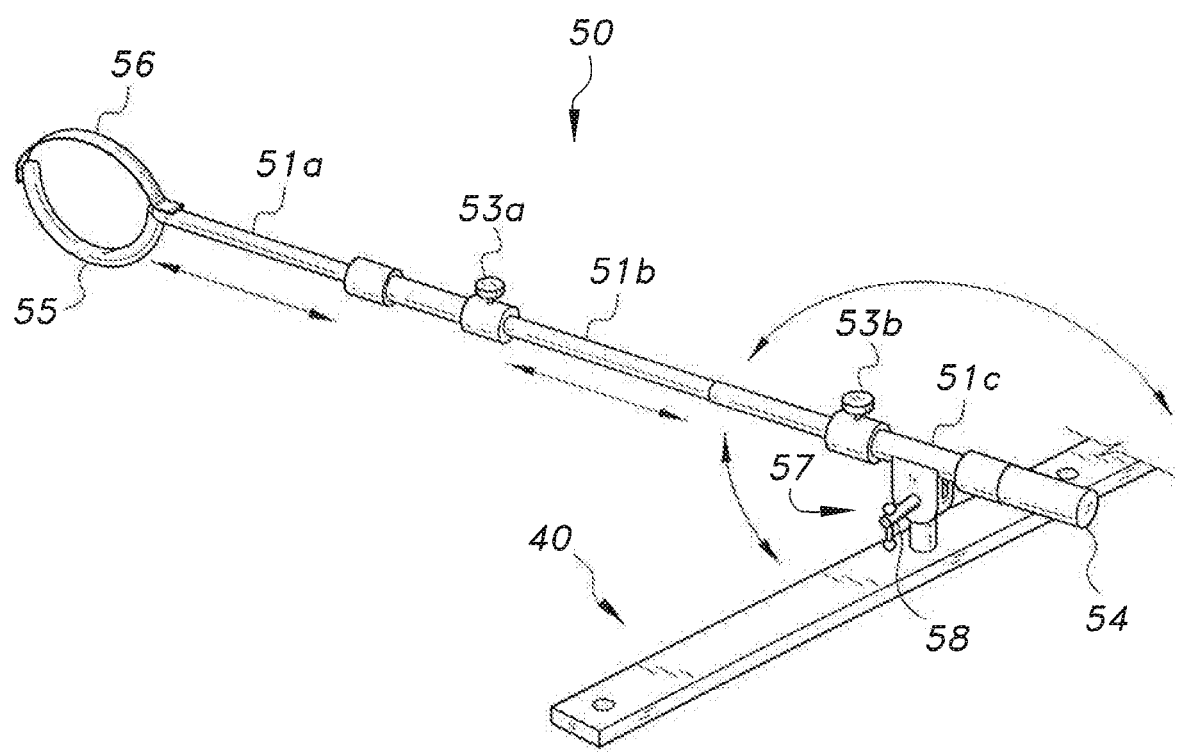
FIG. 3 is a perspective view of one arm of the hip spica cast application device showing a first embodiment of a leg holder.

FIG. 3 illustrates one of the arms 50 and its associated hinge 57 on a device 10 with the platform 60 removed. The hinge 57 is shown connecting the arm 50 to the horizontal member 40. Locking handle 58 on the hinge 57 allows the user to adjust and then lock the hinge 57 at a specific position. In an embodiment, the user can unlock the hinge 57 by rotating the handle 58 counter-clockwise and lock the hinge 57 by rotating the handle 58 clockwise. In such an embodiment, the handle 58 operates two opposing friction plates that lock when pressed together and freely rotate when separated. The handle 58 may be operated in any other suitable manner based on the respective hinge mechanism. Other locking hinges known in the art, which are capable of use as a locking hinge as discussed, are also contemplated.

For example, locking may be accomplished via obstruction by use of opposing sets of teeth or by a peg on one side of the hinge inserted into holes on the opposing side.

It is also contemplated that the arms 50a, 50b have horizontal adjustability. This may be accomplished by slidable attachment of the arms to the horizontal member. For example, a locking mechanism can be provided that allows that arms to slide along the horizontal member 40 and then be locked in place. In such an embodiment, each arm may be connected to the horizontal member 40 by a bracket that extends along the member. A locking screw can be threaded into the bracket and then screwed in to lock the bracket in place by engaging the horizontal member 40. Alternatively, the horizontal adjustability may be achieved by multiple holes defined in the horizontal member. Each arm can be moved to any hole and then locked in place by a bolt through the hole. Additionally, the arm pivots 57 may allow for horizontal adjustability. For example, a double hinge mechanism may be used that has vertical and horizontal locking hinges.

FIG. 3 also details the telescopic mechanism 51. The inner member 51a is designed to extend into the intermediate member 51b until the leg holder 55 prevents further insertion. The arm 50 may be extended out until the end of the inner member reaches the screw 53a. A small flange or other suitable structure may be disposed on the end of the member to catch on the screw and prevent the inner arm from moving past the screw 53a. Preferably, a sufficient portion of the inner member 51a remains in the intermediate member 51b when the arm is fully extended to counter the rotational forces created by the weight of the patient. Intermediate member 51b telescopically engages outer member 51c, similar to inner member 51a and intermediate member 51b.

At the beginning of the hip spica casting procedure, the physician will set the ball at the end of each femur in the patient's respective acetabular sockets and position the legs to hold the ball in the socket. This is the position in which the legs are to be casted for curing the hip dysplasia. It is important that the patient's legs remain in the position set by the physician at the beginning of the hip spica casting procedure during the entire procedure. Hip spica casting is a lengthy procedure which gives the patients leg many opportunities to slide down within the "U" shaped holders 55. Therefore, the strap 56 may be used to lock the patients leg's at a precise position by compressing the leg within the leg holder. The leg holder may be coated with a high friction material so less compression is required to hold the leg in place. In a preferred embodiment, a Velcro (hook and loop fastener) strap 56 is connected to one end of the holder. An opening to receive the Velco strap 56 is located at the other end of the holder. Once the patient's leg is properly positioned in the holder, the strap 56 is fed through the opening in the opposing end of the holder, pulled until taught, and then connected to itself via a Velcro connection, effectively locking the strap in the set position. Other straps known in the art are also contemplated, such as a "belt" connection having holes in the strap through which a member is inserted, or a laced connection that is tied once taught. In some embodiments, the "U" shaped leg holder may be oriented so both ends of the "U" shape are extending out in the same direction as its associated arm. Leg holders known in the art other than that shown may be used. These include a rigid strap that wraps around the leg or a straight post that can be placed under that back of the knee.

FIG. 4 shows the cast application device 10 pivoted to extend upwards. The position of the arms 50 during casting may be determined on a case by case basis, based on the needs of the patient. The height of the post may be adjusted to align the platform 60 with an upper surface of a table 70. As a result, the platform 60 can be configured to lie parallel to and substantially in plane with the table 70. The arms 50 can be lengthened based on the location of the base 30 in relation to the patient, and a space needed for the physician to perform the procedure. Additionally, the arms 50 can be angled outwards to widen the distance between the leg holders and accommodate any necessary angular deviations.

Figure 5:
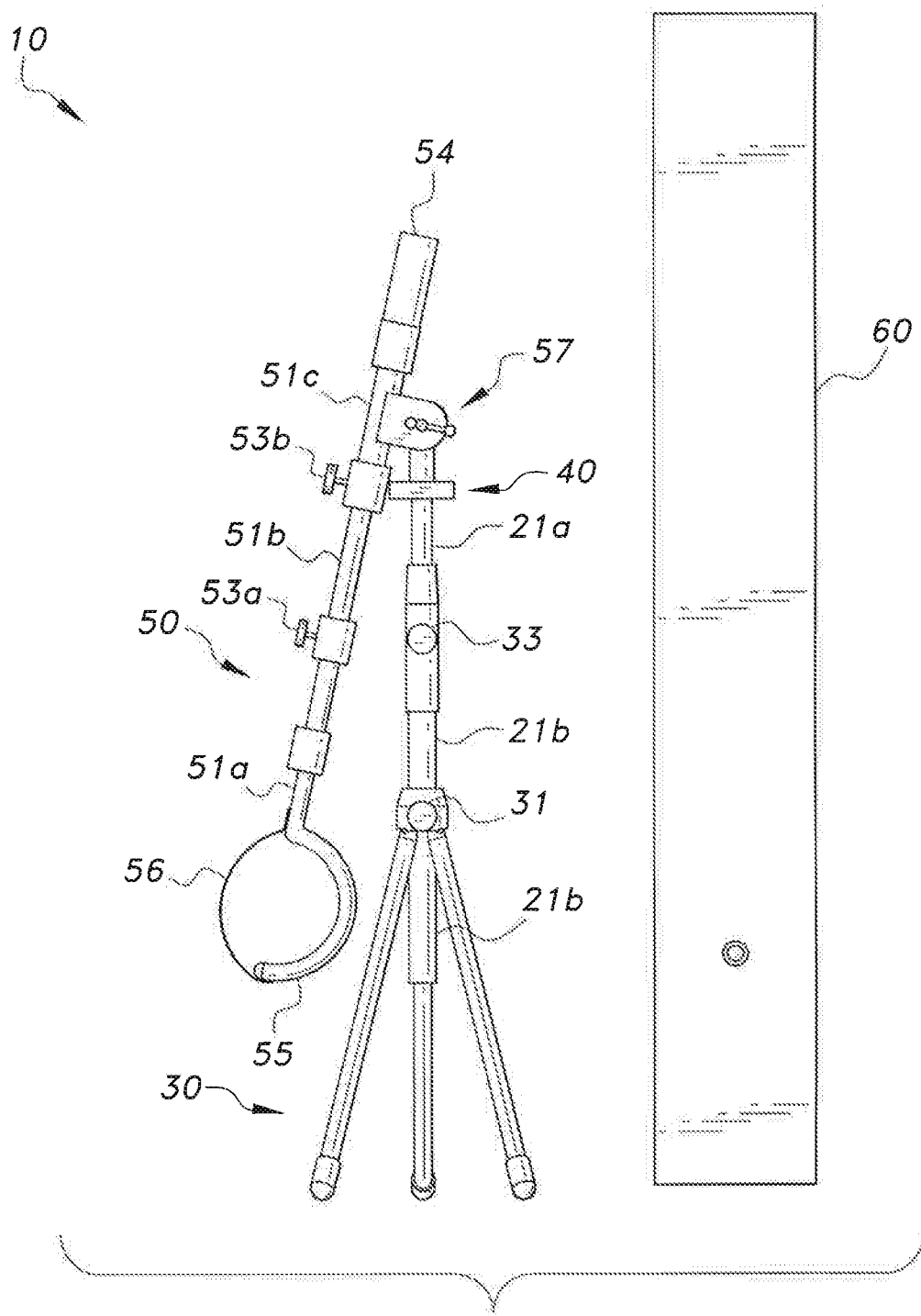
FIG. 5 is an isometric side view of the hip spica cast application device in a storage position.

FIG. 5 shows the cast application device 10 in a storage configuration. Hip spica casting may not be a common procedure, therefore dedicating a full room or large space to a casting table may not be within the best interests of an organization. The present device 10 is capable of being configured in a storage or folded position to occupy less space and facilitate movement thereof. As shown in FIG. 5, both arms 50 and the post 20 can be fully retracted, and arms 50 can also be angled downward. The base 30 may be contracted by loosening screw 31, folding in the legs of the base, and sliding the base 30 up the outer member 21b of the post 20. Additionally, the platform 60 may be removed and stood next to the remainder of the device 10 by simply unscrewing screw 64. In this configuration, the device takes up a small portion of the space compared to the device in a casting position.

To convert the cast application device 10 from a storage position into a casting position, a user may first attach the platform 60 to the horizontal member 40 using screw 64. Then, a user may pull the hinge locking lever 58 on each arm 50a, 50b to unlock the arm hinges 57a, 57b. Once the hinges 57a, 57b are unlocked, the arms 50a, 50b can be rotated up to an upward orientation using the handles 54a, 54b. The arms 50a, 50b can be lengthened by loosening the locking screws 53a, 53b on each arm, pulling out the inner and intermediate member 51a, 51b of the arms 50a, 50b, and them tightening the locking screws 53a, 53b when the arms are at a desired length. At this point, the post 20 can be adjusted to align the lower surface of the platform 60 with the top surface of the table 70 and the device 10 can be positioned so the terminal end of the long side of the platform 60 rests on the table 70. In some embodiments, a strap 62 of the platform 60 may be wrapped around the table 70 for additional securement between the platform 60 and table 70.

Figure 6:
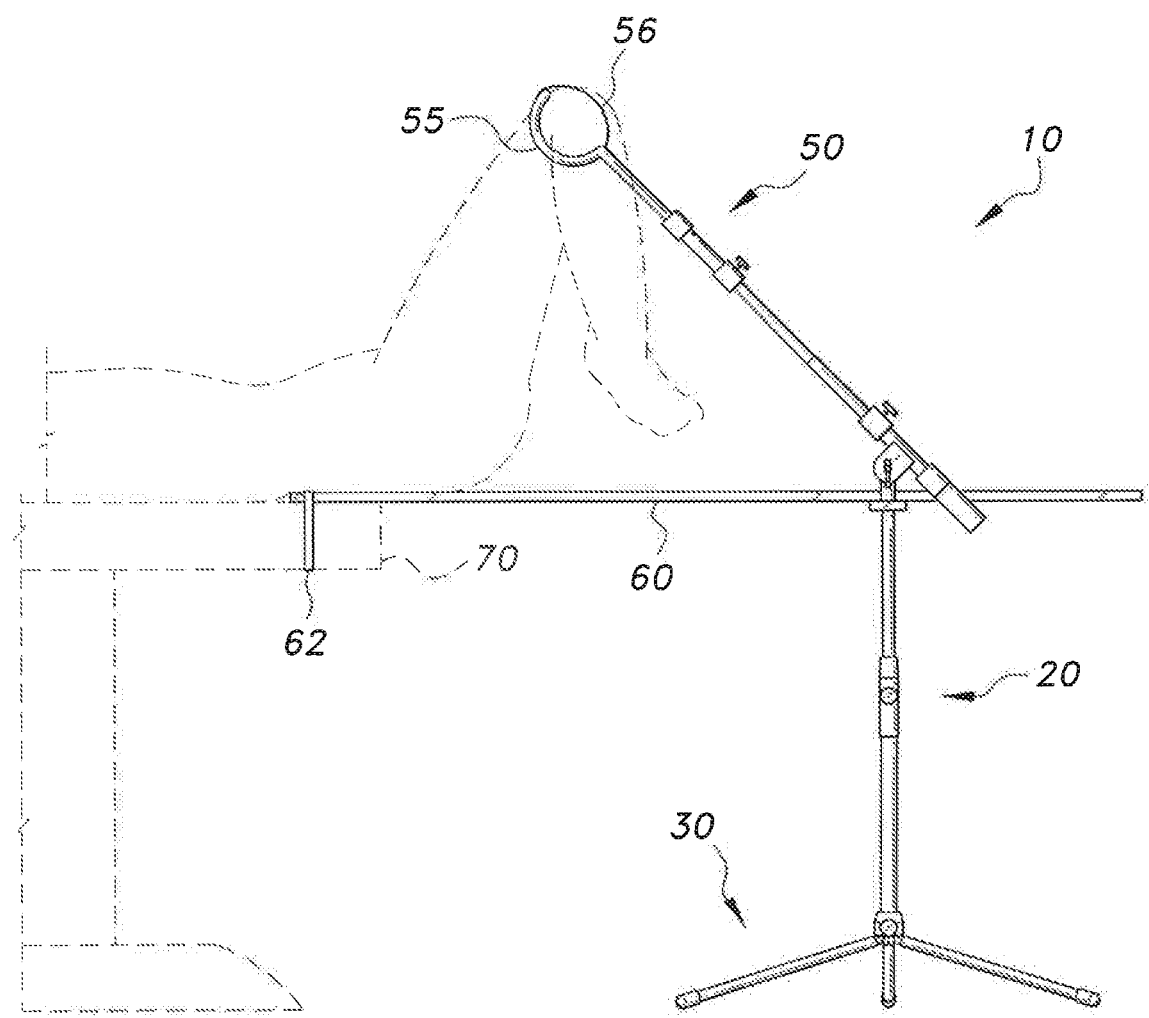
FIG. 6 is an environmental side view of the hip spica cast application device in a casting position show in a first configuration.

FIGS. 1 and 6 show a configuration of the hip spica casting device 10 in use. As shown in FIG. 1, a patient's upper back is resting on the table 70, the patient's lower back and buttock are resting on the platform 60, and the patient's legs are being supported by the arms 50 of the cast application device 10. A majority of the patient's weight is held by the table 70, which can be an exam table, a surgical table, or an orthopedic table, and the platform 60. Any surface capable of holding the patient and platform 60 in a horizontal position may be used in place of the table 70. In some non-limiting embodiments, the table 70 may have an adjustable height.

After the patient is appropriately positioned on the table 70 and the platform 60, the practitioner may adjust the patients hip joins to a position which properly sets the femoral balls into their respective acetabular sockets. Once the hips are appropriately positioned, the practitioner or an assistant may adjust the arms 50 so the "U" shaped leg holders 55 hold the legs, and associated hip joints, at the desired position. The straps 56 spanning the open end of the led holders 55 are tightened around the patient's legs to ensure the legs do not shift. The leg holders 55 can be attached to any point along the length of the thigh. At this point, the physician may confirm that the patient's legs are in the proper position to be casted. If the position needs to be altered, the device 10 may be adjusted to the appropriate position without disconnecting the patient.

Figure 7:
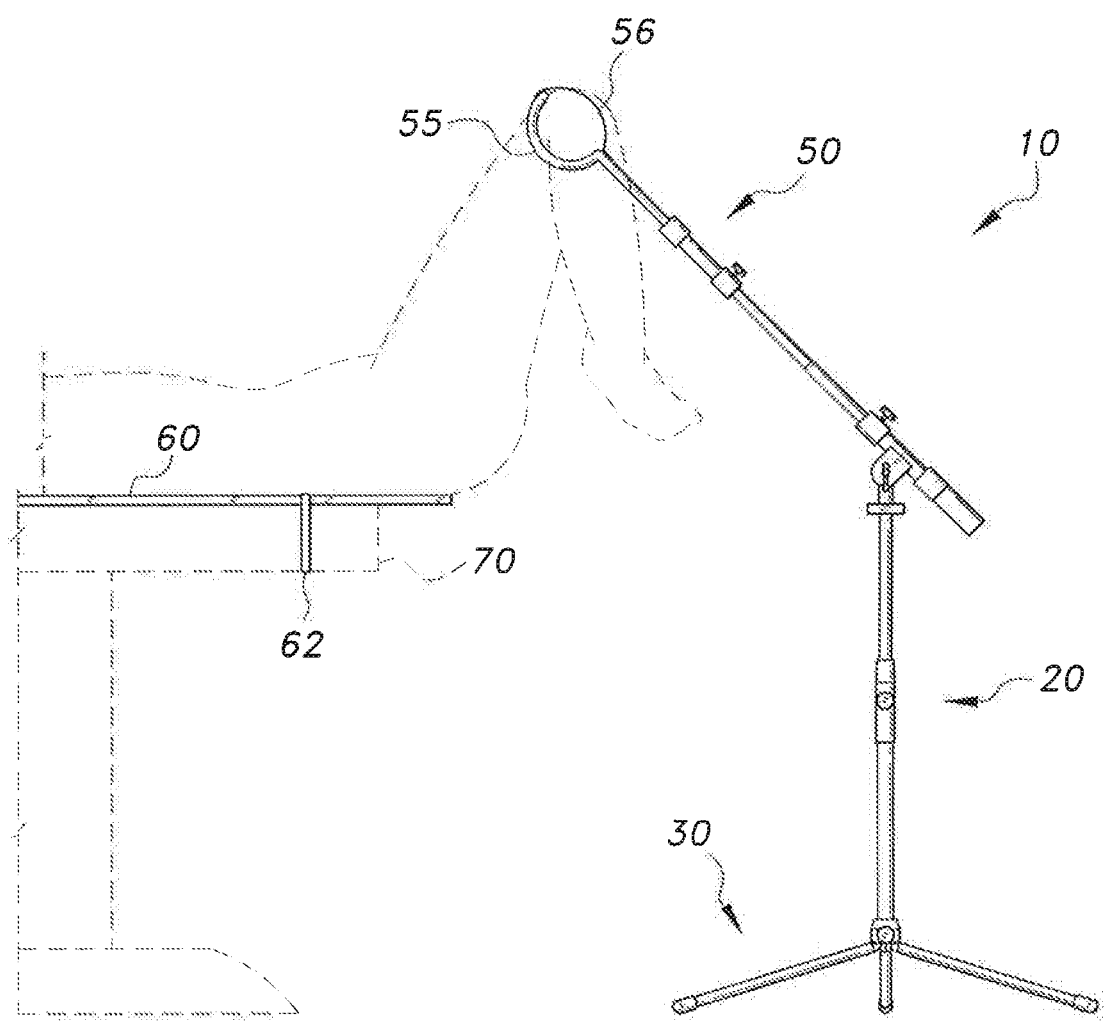
FIG. 7 is an environmental side view of the hip spica cast application device in a casting position show in a second configuration.

FIG. 7 shows an embodiment of the hip spica cast application device 10 with a detachable platform 60. As shown, platform 60 is detached from the device 10 and secured only to the table 70. The platform is resting on the table 70 with a portion of the platform 60 extending over the edge of the table 70. A strap 62 may be provided to further secure the platform 60 to the table 70.

The cast application device may be made of any suitable material known in the art. Exemplary metals may include steel, titanium, aluminum, iron, or alloys thereof. Exemplary polymers may include polyethylene, polyvinyl chloride, polyoxymethylene, acrylonitrile butadiene styrene, or copolymers thereof. It is contemplated that different components of the device 10 may be made by different materials based on the demands of the component.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A hip spica cast application device, consisting of:
   a base;
   a post extending from the base, the post having a lower end and an opposing top end and having a selectively adjustable vertical length;
   an elongated, rectangular horizontal member attached to and extending in a horizontal plane to the top end of the post, the horizontal member having a top surface and a bottom surface, wherein the top end of the post is attached to the bottom surface of the horizontal member;
   a pair of spaced, telescopic arms rotatably and pivotally connected by a rotatable and pivotal connection to the top surface of the horizontal member such that the arms are spaced from either side of the post, wherein the rotatable connection provides for rotation is about a vertical plane and the horizontal connection provides for pivoting about a horizontal plane, each of the pair of spaced arms having a first end and an opposed second end and further having a selectively adjustable length;
   a platform removably attached to and extending perpendicularly and horizontally from the horizontal member, the platform being disposed between the pair of spaced arms; and
   a leg holder at the first end of each of the spaced arms, each leg holder including at least one fastener adapted to be secured to a thigh of a patient thereby holding the patient in a reduced position so the hips do not lose a necessary reduction, thereby allowing a physician to wrap a cast around the hip and lower extremities while they are held in the reduced position.

2. The hip spica cast application device according to claim 1, wherein the at least one fastener is selected from the group consisting of a hook-and-loop fastening strap, a cord, and a belt.

3. The hip spica cast application device according to claim 2, further comprising compressible padding disposed along each leg holder.

4. The hip spica cast application device according to claim 2, wherein each arm further comprise a handle at a second end thereof.

5. The hip spica cast application device according to claim 4, further comprising a joint between each arm and the horizontal member, each joint configured to be locked and unlocked by operation of the respective handle.

6. The hip spica cast application device according to claim 1, wherein each of the telescopic arm comprises: i) an inner member and an intermediate member, the intermediate member telescopically receiving the inner member; and ii) a pair of first locking screws, each first locking screw extending through and threadedly engaging a respective intermediate member.

* * * * *